US011565019B2

(12) United States Patent
Campos Cuerva et al.

(10) Patent No.: US 11,565,019 B2
(45) Date of Patent: Jan. 31, 2023

(54) HEMOSTATIC EFFICACY OF A NANOSTRUCTURED FIBRIN AGAROSE HYDROGEL

(71) Applicants: FUNDACIÓN PÚBLICA ANDALUZA PROGRESO Y SALUD, Seville (ES); SERVICIO ANDALUZ DE SALUD, Seville (ES)

(72) Inventors: Rafael Campos Cuerva, Seville (ES); Beatriz Fernandez Muñoz, Seville (ES); Miguel Angel Gómez Bravo, Seville (ES); Carmen Cepeda Franco, Seville (ES); Jordi Muntane Relat, Seville (ES)

(73) Assignees: FUNDACIÓN PÚBLICA ANDALUZA PROGRESO Y SALUD, Seville (ES); SERVICIO ANDALUZ DE SALUD, Seville (ES)

( * ) Notice: Subject to any disclaimer, the term of this patent is extended or adjusted under 35 U.S.C. 154(b) by 83 days.

(21) Appl. No.: 17/045,661

(22) PCT Filed: Apr. 8, 2019

(86) PCT No.: PCT/EP2019/058822
§ 371 (c)(1),
(2) Date: Oct. 6, 2020

(87) PCT Pub. No.: WO2019/193202
PCT Pub. Date: Oct. 10, 2019

(65) Prior Publication Data
US 2021/0154352 A1    May 27, 2021

(30) Foreign Application Priority Data

Apr. 6, 2018 (ES) ............................... ES201830346
Sep. 6, 2018 (ES) ............................... ES201830872

(51) Int. Cl.
*A61L 24/00* (2006.01)
*A61L 24/04* (2006.01)
*A61L 26/00* (2006.01)
*A61L 31/14* (2006.01)

(52) U.S. Cl.
CPC ....... *A61L 24/0042* (2013.01); *A61L 24/0031* (2013.01); *A61L 24/043* (2013.01); *A61L 26/008* (2013.01); *A61L 26/009* (2013.01); *A61L 26/0052* (2013.01); *A61L 31/145* (2013.01); *A61L 31/148* (2013.01); *A61L 2400/04* (2013.01); *A61L 2400/12* (2013.01)

(58) Field of Classification Search
None
See application file for complete search history.

(56) References Cited

FOREIGN PATENT DOCUMENTS

| EP | 2 471 902 A2 | 4/2012 |
|---|---|---|
| WO | 2011/123346 A1 | 10/2011 |

OTHER PUBLICATIONS

Campos et al., "Ex vivo characterization of a novel tissue-like cross-linked fibrin-agarose hydrogel for tissue engineering applications", Biomed. Mater., vol. 11, 2016.*
Alaminos et al., "Construction of a Complete Rabbit Cornea Substitute Using a Fibrin-Agarose Scaffold," *Investigative Ophthalmology & Visual Science* 47(8):3311-3317, Aug. 2006.
Berrevoet et al., "Clinical Application of Topical Sealants in Liver Surgery: Does it Work ?," *Acta Chir Belg* 107(5):504-507, 2007.
Brustia et al., "An update on topical haemostatic agents in liver surgery: systematic review and meta analysis," *J Hepatobiliary Pancreat Sci*, 2016, (13 pages).
Campos-Cuerva et al., "Nanostructured fibrin agarose hydrogel as a novel haemostatic agent," *J Tissue Eng Regen Med.* 13:664-673, 2019.
Carriel et al., "Combination of fibrin-agarose hydrogels and adipose-derived mesenchymal stem cells for peripheral nerve regeneration," *J. Neural Eng.* 10(026022), 2013, (15 pages).
Carriel et al., "Epithelial and Stromal Developmental Patterns in a Novel Substitute of the Human Skin Generated with Fibrin-Agarose Biomaterials," *Cells Tissues Organs* 196:1-12, 2012.
Carriel et al., "In vitro characterization of a nanostructured fibrin agarose bio-artificial nerve substitute," *J Eng Regen Med* 11:1412-1426, Jul. 14, 2015.
Carriel et al., "Tissue engineering of the peripheral nervous system," *Expert Review of Neurotherapeutics* 14(3):301-318, 2017.
Codispoti et al., "Individualized Heparin and Protamine Management in Infants and Children Undergoing Cardiac Operations," *Ann Thorac Surg* 71:922-928, 2001.
Eeson et al., "Hemostasis and Hepatic Surgery," *Surg Clin N Am* 96, 2016, (10 pages).
Galanakis et al., "A Review of Current Hemostatic Agents and Tissue Sealants Used in Laparoscopic Partial Nephrectomy," *Reviews in Urology* 13(3):131-138, 2011.

(Continued)

*Primary Examiner* — Robert A Wax
*Assistant Examiner* — Randeep Singh
(74) *Attorney, Agent, or Firm* — Seed Intellectual Property Law Group LLP (57) ABSTRACT

The present invention provides for nanostructured fibrin and agarose hydrogels, preferably type VII agarose hydrogels, (NFAH) or non-nanostructured or pre-nanostructured fibrin and agarose hydrogels, preferably type VII agarose hydrogels, (FAH), as hemostatic agents designed for use as an adjunct or primary treatment in moderate intraoperative hemorrhage and in trauma. These hydrogels can be applied topically to the wound either on the skin in a laparotomy or as non-invasive manner in surgical procedures. Its nanostructure technology generates an adhesive stable fibrin clot required for hemostasis. The attachment properties of the hydrogel, as well as the rapid formation of a fibrin clot, ensures that a strong stable fibrin clot is formed shortly after application.

14 Claims, 9 Drawing Sheets

(56) References Cited

OTHER PUBLICATIONS

Garzon et al., "Generation of a biomimetic human artificial cornea model using Wharton's jelly mesenchymal stem cells," *IOVS*, Jun. 6, 2014, (29 pages).
Moggia et al., "Methods to decrease blood loss during liver resection: a network meta-analysis (Review)," *Cochrane Database of Systematic Reviews* 10(CD010683), 2016, (381 pages).
Mosesson et al., "The Structure and Biological Features of Fibrinogen and Fibrin," *Annals of the New York Academy of Sciences* 936(1):Jun. 11-30, 2006.
Scionti et al., "Effect of the hydration on the biomechanical properties in a fibrin-agarose tissue-like model," *J Biomed Mater Res Part A* 2013(00A), 2013, (10 pages)I.
Scionti et al., "Effect of the hydration on the biomechanical properties in a fibrin-agarose tissue-like model," *J Biomed Mater Res Part A* 2014 (102A):2573-2582, 2014.
Spotnitz, "Fibrin Sealant: The Only Approved Hemostat, Sealant, and Adhesive—a Laboratory and Clinical Perspective," *ISRN Surgery* 2014(203943), Mar. 4, 2014, (28 pages).
2022/0009993, Jan 13, 2022.
2021/0207089A1, Jul. 8, 2021.
U.S. Pat. No. 10,960,011, Mar. 30, 2021.
2022/0142985, May 12, 2022.
U.S. Pat. No. 11,344,260, May 31, 2022.
2021/0207089, Jul. 8, 2021.
2022/0170019, Jun. 2, 2022.
U.S. Appl. No. 17/641,735, filed Mar. 9, 2022.
2022/0043006, Feb. 10, 2022.
2019/0331684, Oct. 31, 2019.
U.S. Appl. No. 17/611,460, filed Nov. 15, 2021.

\* cited by examiner

Inflammatory factors in 0.5 cm hepatic resection

Fig. 9

Inflammatory factors in 1.5 cm hepatic resection

Histological analysis of 0,5 cm hepatic resection

Histological analysis of 1,5 cm hepatic resection

HEMOSTATIC EFFICACY OF A NANOSTRUCTURED FIBRIN AGAROSE HYDROGEL

TECHNICAL FIELD OF THE INVENTION

The present invention relates to the application as an adhesive sealant component and hemostatic agent of nanostructured fibrin and agarose hydrogels, preferably type VII agarose hydrogels (NFAH). Such nanostructured fibrin and agarose hydrogels, preferably type VII agarose hydrogels (NFAH), may be use to stop bleeding or seal tissue in vivo with and without compression. This invention is particularly related to a need of incorporating a fibrin sealant in a viscous gel-like product that can resist the flow of blood in a wound in order to seal tissue and control vascular, epidermal, bone, or internal hemorrhage.

BACKGROUND OF THE INVENTION

Uncontrolled hemorrhage continues to be an important concern in surgical interventions and is responsible for higher rates of mortality, morbidity and longer hospital stays (Brustia, Granger, & Scatton, 2016). Injury of blood vessels triggers different mechanisms in order to establish a complex process called hemostasis. Hemostasis is an interruption of the escape of blood by either natural or artificial means.

Hepatic resection usually requires a perioperative transfusion due to intraoperative blood loss in patients. There are several surgical techniques used to reduce bleeding (Berrevoet & De Hemptinne, 2007). These methods however have a transitory or incomplete effect. This in turn requires a topical haemostatic agent to prevent postoperative blood loss (Moggia et al., 2016) (Eeson & Karanicolas, 2016).

Different hemostatic agents approved by Food and Drug Administration (FDA) are used in multiple surgical disciplines to reach hemostasis. Among these, fibrin sealant derived from human plasma has become a thriving hemostatic agent due to its capacity to imitate and promote the final step of coagulation cascade to assist hemostasis (MOSESSON, SIEBENLIST, & MEH, 2006) (Mankad & Codispoti, n.d.). It also reduces potential rejection and undesirable effects, and is the only FDA clinical material approved as hemostats, sealants and adhesives (Spotnitz, 2014). Despite advantages in the field, time to hemostasis, applicability and postoperative transfusion can further be improved.

A recent nanostructured fibrin and type VII agarose hydrogel (NFAH) was developed as biomaterial to use in multiple biocompatible models (Carrie) et al., 2017). This tissue-like substitute is mainly composed of human plasma and shows highly flexible and elastic properties as well as mechanical strength (MOSESSON et al., 2006; Scionti et al., 2014).

This invention focuses on the hemostatic effectiveness of agarose hydrogels, preferably type VII agarose hydrogels (NFAH), and illustrates such effectiveness in an in vivo model. To this purpose, NFAH was compared with two commercially available hemostatic products used in multiple surgical disciplines: Hemopatch, a polyethylene glycol-coated collagen pad and Tachosil, a fibrinogen and thrombin-coated collagen pad.

SUMMARY OF THE INVENTION

The present invention lies within the domain of biological tissue sealants and hemostats, which are biodegradable and nontoxic, intended for therapeutic use, for example, as an adjunct to hemostasis in laparotomy or laparoscopic surgery, in orthopedic surgery, trauma (spleen laceration or hepatic surgery), and large-bed wounds.

In one aspect, the present invention relates to biocompatible adhesive nanostructured fibrin and agarose hydrogels, preferably type VII agarose hydrogels (NFAH), which are bio-reabsorbable and nontoxic, for surgical or therapeutic use. It also relates to a single-part application containing a nanostructured fibrin and a agarose hydrogel, preferably a type VII agarose hydrogel (NFAH), which can be released in a given site to produce a stable fibrin clot.

In vivo studies shown herein illustrate that nanostructured fibrin and agarose hydrogels, preferably type VII agarose hydrogels (NFAH), are an excellent general hemostatic agent candidate for use as adjunct and primary treatment in moderate bleeding. The agent is durable, easy to store, poses minimal risk, requires little training to use, and is highly effective against bleeding.

DETAILED DESCRIPTION

In the present invention, we investigated the hemostatic success of a cellularized NFAH (c-NFAH) in partial hepatectomy in rats. The findings showed that c-NFAH has greater hemostatic success than commercially available hemostatic agent Hemopatch. Such promising results prompted us to extend the experiments increasing the length of hepatic section and including other hemostatic agents. To this end, TachoSil was incorporated to the study owing to its similar composition in respect to the NFAH under investigation. An acellularized NFAH (a-NFAH) was also included in order to check if lower time of hemostasis was mainly due to NFAH composition rather than by the presence of cells. One more time, results showed NFAH have lower time to hemostasis than Hemopatch. Moreover, this effectiveness of NFAH in reaching hemostasis was also significantly superior to Tachosil. In this study, Hemopatch was also found to have a greater success than Tachosil in achieving immediate hemostasis in hepatic surgical model.

In addition, although as shown in the examples, hemostatic pads need a long time of local compression in order to reach hemostasis, NFAH placement on sectinated liver was enough to act as hemostatic agent. This different application procedure confers a great advantage to NFAH avoiding mechanical compressions that cause hematomas.

Also, NFAH treatment groups, unlike Hemopatch and Tachosil, showed no incidences of hematoma in any hepatic resection size. These results are probably due to the lower time to hemostasis of NFAH treatments and its easier applicability avoiding the hematoma formation.

Also, the low grade of adhesion produced by NFAH pads compared to hemostatic agents Hemopatch and Tachosil is also a remarkable aspect. This attribute can be an important advantage to its use in any surgical application.

Moreover, postoperative re-bleeding were found in any treatment group as expected and the only migrated pad found in Tachosil treatment group was probably due to an involuntary change of position during the suture.

On the other hand, no significant differences were observed in CRP and IL-1β levels between c-NFAH and Hemopatch in 0.5 cm hepatic resections. However, these results were not reproducible in 1.5 cm resections. In 1.5 cm hepatic resections, there was not an only treatment with the lowest levels in all inflammatory factors analyzed. Firstly, lowest CRP level was obtained with Tachosil treatment, but a-NFAH showed no significant differences with Hemopatch; secondly, Tachosil produced the lowest IL-1β level with no significant differences with NFAH treatments; and finally, Hemopatch group had the lowest TNF-α levels with no significant differences with a-NFAH.

Although results showed higher level of CRP in c-NFAH with respect to a-NFAH, probably due to the presence of cells that caused higher immunity response, IL-1β and TNF-α levels were not significantly different.

In conclusion, a-NFAH treatment had at least no higher inflammatory levels with respect to commercially available hemostatic agents included in this study. These findings indicate that a-NFAH is a safe product with no higher inflammatory response. In general, NFAH treatments showed better histological results than commercially hemostatic agents under study. In 1.5 cm hepatic resections, the best hemorrhage, inflammation and necrosis results were obtained by a NFAH treatment. Only c-NFAH had higher presence of neutrophil granulocytes and necrosis in 0.5 cm hepatic resection.

On the basis of the above results, NFAH (a-NFAH as well as c-NFAH) is described in the present invention, for the first time, as a hemostatic agent and tissue sealant, for use as an adjunct to hemostasis or primary treatment in surgical procedures and in treatment of traumatic wounds. Such results can be extrapolated to agarose hydrogels in general for use as an adjunct to hemostasis or primary treatment in surgical procedures and in treatment of traumatic wounds. It is noted, that agarose is thermo-reversible and can be modified to melt and gel at a variety of temperatures. This allows the gel to be used in myriad applications across fields as diverse as the food industry, molecular biology, cell biology, and tissue engineering. Agarose hydrogels are preferably understood in the context of the present invention as thermosensitive hydrogels that have a melting temperature at around 40° C. and a gelling temperature at approximately 32° C., making this hydrogel suitable for in vitro and in vivo applications. Because of this thermal gelation properties, agarose has the added advantage or requiring no additional crosslinking step.

It is noted that NFAH can be made as described in any of the protocols reported in the prior art (Alaminos, M., Sanchez-Quevedo, M. C., Munoz-Avila, J. I., Serrano, D., Medialdea, S., Carreras, I., Campos, A., 2006. Construction of a complete rabbit cornea substitute using a fibrin-agarosescaffold. Invest. Ophth. Vis. Sci. 47, 3311-3317; Carriel V, Alaminos M, Garzon I et al. 2014a; Tissue engineering of the peripheral nervous system. Expert Rev Neurother 14: 301-318; Carriel V, Garrido-Gomez J, Hernandez-Cortes P et al. 2013; Combination of fibrin-agarose hydrogels and adipose-derived mesenchymal stem cells for peripheral nerve regeneration. J Neural Eng 10: 026022; Carriel V, Garzon I, Jimenez J M et al 0.2012; Epithelial and stromal developmental patterns in a novel substitute of the human skin generated with fibrin-agarose biomaterials. Cells Tissues Organs 196:1-12; Garzon I, Martin-Piedra M A, Alfonso-Rodriguez C et al. 2014; Generation of a biomimetic human artificial cornea model using Wharton's jelly mesenchymal stem cells. Invest Ophthalmol Vis Sci 55: 4073-4083; Scionti G, Moral M, Toledano M et al 0.2013; Effect of the hydration on the biomechanical properties in afibrin-agarose tissue-like model. J Biomed Mater Res A102 (8): 2573-2582) or as described in the examples illustrated in the present invention.

Figure 13:
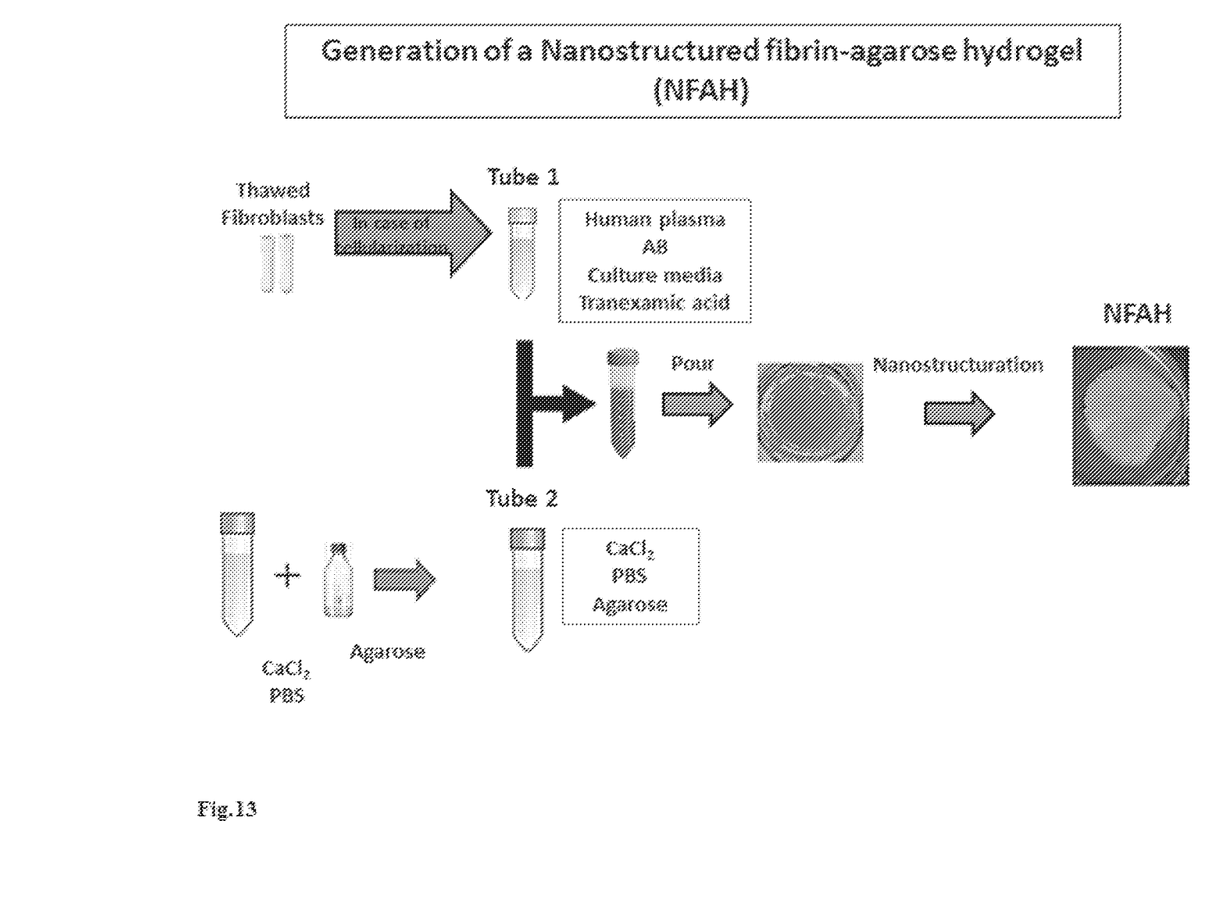
FIG. 13. Generation of nanostructured fibrin-agarose hydrogel (NFAH)

Particularly, and as shown in FIG. 13, for cellularized NFAH fabrication, human fibroblasts are previously thawed and momentarily kept in culture media in a specific number of cells. First, a Tube 1 is prepared adding human plasma, tranexamic acid and culture media with or without cells (for acellularized NFAH (a-NFAH) manufacturing, the volume of culture media added to the mix will be the same but does not contains cells). Once tube 1 is ready, this is kept at 37° C. Separately, a tube 2 is prepared by addition of calcium chloride (CaCl$_2$) and Phosphate-Buffered Saline (PBS). After this, a 2.2% agarose solution is warmed at 39-41° C. and added to a tube 2 and mixed. Immediately, tube 1 solution is added to tube 2, mixed and poured on a well. After 2 hours at room temperature, the fibrin-agarose hydrogel (FAH) obtained is kept with culture media in the incubator for at least 24 hours. Nanostructuration is the last step to obtain a nanostructured fibrin-agarose hydrogel (NFAH). This process consists in a compression and dehydration of FAH. To this end, FAH is placed between nylon net filters. Blotting filter papers are then placed on nylon filters and nanostructuration is performed by application of a flat glass with a specific weight and surface.

Other types of agarose hydrogels different from those using type VII agarose might be prepared in a similar fashion as explained above.

Therefore a first aspect of the present invention refers to a composition for use in the control of bleeding with or without compression comprising nanostructured fibrin and an agarose hydrogel, preferably a type VII agarose hydrogel, (NFAH) or a non-nanostructured or a pre-nanostructured fibrin and an agarose hydrogel, preferably a type VII agarose hydrogel, (FAH). Preferably, this composition is intended for use as biological tissue sealants and hemostats, which are, more preferably, biodegradable and non-toxic. More preferably, this composition is intended for therapeutic use, for example, as an adjunct to hemostasis in laparotomy or laparoscopic surgery, in orthopedic surgery, trauma (spleen laceration or hepatic surgery), and large-bed wounds. Still more preferably, this composition is intended for use as a general hemostatic agent candidate for use as adjunct and/or primary treatment in moderate bleeding. The composition is durable, easy to store, poses minimal risk, requires little training to use, and is highly effective against bleeding.

In a preferred embodiment of the first aspect of the invention, the composition for use is preferably cellularized nanostructured fibrin and agarose hydrogels, preferably type VII agarose hydrogels, (c-NFAH) or non-nanostructured or pre-nanostructured fibrin and agarose hydrogels, preferably type VII agarose hydrogels, (c-FAH).

In another preferred embodiment of the first aspect of the invention, the composition for use is preferably acellularized (without cells) nanostructured fibrin and agarose hydrogels, preferably type VII agarose hydrogels, (a-NFAH) or non-nanostructured or pre-nanostructured fibrin and agarose hydrogels, preferably type VII agarose hydrogels, (a-FAH).

The composition for use according to the first aspect of the invention, wherein for the cellularized NFAH fabrication, human fibroblasts are preferably previously thawed and kept in culture media in a specific number of cells. Then, a Tube 1 is prepared by adding fibrin, preferably human plasma and tranexamic acid, and culture media with or without cells. Once tube 1 is ready, this is preferably kept at 37° C. Separately, a tube 2 is prepared by addition of jellification agent such as calcium chloride (CaCl2)) and Phosphate-Buffered Saline (PBS). After this, a 2.2% agarose solution is warmed at 39-41° C. and added to a tube 2 and mixed. Preferably immediately, tube 1 solution is added to tube 2, mixed and poured on a well. After approximately 2 hours at room temperature, the fibrin-agarose hydrogel (FAH) obtained is kept with culture media in the incubator for at least 24 hours. Nanostructuration is the last step to obtain a nanostructured fibrin-agarose hydrogel (NFAH). This process consists in a compression and dehydration of FAH. To this end, FAH is preferably placed between nylon net filters. Blotting filter papers are then placed on nylon filters and nanostructuration is performed by application of a flat glass with a specific weight and surface.

The composition for use according to the first aspect of the invention, wherein for acellularized NFAH (a-NFAH) manufacturing, the volume of culture media added to the mix will be the same as the one added for the cellularized NFAH but without cells.

The composition for use according to the first aspect of the invention, wherein for acellularized FAH or cellularized FAH manufacturing, the information is clearly derivable from the above paragraphs.

EXAMPLES

Materials and Methods
Hemostatic Agents

Four different hemostatic agents were used in this study: two commercially available, Hemopatch® and Tachosil®, and two home-made NFAH, a cellular NFAH (c-NFAH) and an acellular NFAH (a-NFAH).

Hemopatch (Baxter AG, Vienna, Austria) is a collagen pad derived from bovine dermis with an active side coated with a protein reactive pentaerythritol polyethylene glycol ether tera-succinimidyl glutarate (TACHOSIL, 2010)

Tachosil (Takeda Austria Gmbh) is an equine collagen sponge with an active side coated with human derived fibrinogen (5.5 mg/cm2) and thrombin (2.0 IU/cm2)

NFAH is a high-density fibrin-type VII agarose hydrogel with approximately 80% of hydration and 50-60 µm thickness Cell Culture Fibroblasts used in this study were isolated from rat tissue. Skin rat biopsies were thoroughly washed in 1× phosphate buffered saline (PBS) with an antibiotic-antimycotic cocktail solution (100 U/ml penicillin G, 100 µg/ml streptomycin, 20 µg/ml gentamicin and 50 µg/ml vancomycin) and fragmentized in pieces of approximately 1×1 mm. Approximately, twenty pieces were transferred to a 50 mL conical centrifuge tube containing 5 mL of preheated collagenase solution (2 mg/mL of collagenase (SERVA Electrophoresis Gmbh) prepared in Dulbecco's modified Eagle's medium (DMEM). Samples were incubated 16 hours at 37° C.

Digestion was neutralized by addition of 25 mL culture media (DMEM supplemented with 10% fetal bovine serum, 0.1 mM non-essential amino acid, 2 mM Glutamax, 100 U/ml penicillin G and 100 µg/ml streptomycin). Finally, cells suspension was centrifuged, counted, plated in a 6-well plate and grown in a humidified incubator at 5% CO2 and 37° C.

Media was changed every 2-3 days until the culture reached 70-90% confluence. At this point, cells were subsequently harvested and expanded. Finally, cells were cryopreservated and kept in liquid nitrogen until generation of hydrogel.

Immunofluorescence

Cells were seeded onto glass coverslips (VWR) in 24 well plates (Nunc) and incubated a humidified incubator at 5% $CO_2$ and 37° C. Once cell culture reaches confluence, coverslips were washed with PBS and fixed with 3.7% formaldehyde (Sigma) in PBS for 15 min at room temperature. After fixing, cells were washed 3 times with PBS, permeabilized with 0.05% Triton X-100 (Sigma) for 15 min at room temperature, and blocked with PBS containing 1% BSA for 30 minutes at 37° C. Then, cells were separately incubated for 30 minutes at 37° C. with the indicated dilution of the primary antibodies. All primary antibodies were diluted in PBS containing 0.1% BSA. Once primary antibodies were incubated, coverslips were washed 3 times with PBS and incubated for 30 minutes at 37° C. with secondary antibody. Nuclei were stained with a 1 µg/ml solution of 4',6-diamino-2-phenilindole (DAPI; Life technologies). Then, coverslips with the stained cells were mounted with Prolong mounting reagent (Life technologies). Fluorescent microscopy was performed in a TiS microscope (Nikon).

Karyotyping

G-banding Karyotyping of the fibroblast line was performed by the Andalusian Public Health System Biobank following recommendations of the International Standing Committee on Human Cytogenetic Nomenclature (2013).

Generation of NFAH Pad

The protocol is an adaptation of methods reported in previous reports (Alaminos et al., 2006; Carriel et al., 2012, 2013; Scionti et al., 2013; Garzon et al., 2014; Carriel et al., 2015). In order to obtain the volume of fibrin and agarose hydrogel (FAH) for a 6 well plate, a 30 ml mixture was prepared as follows: 25 ml of human plasma, 0.5 ml of tranexamic acid and 2 ml of culture media with or without human fibroblasts were placed into a Falcon tube (cellularized solution was prepared with 150.000 thawed cells per ml of final volume). Subsequently, a solution containing 1.8 ml calcium chloride 10%, 1.2 ml PBS and 2.2% melted type VII-agarose were added. After mixing, 5 ml of solution was place into each well and kept at 37° C. for 2 hours. Once gelation was completed, FAH was covered with culture media and kept at 37° C. for 24 hours until nanostructuration. If FAH contained cells, plates remained in the incubator for 7 days.

Nanostructuration is a compression and dehydration process. To this aim, FAH was placed between a couple of 10 µm nylon net filter (Merck-Millipore) and compressed by extra thick western blotting filter paper (Thermo Scientific) under a flat glass surface of 500 gr for 1 minute and 40 seconds. A final NFAH is obtained with a high-density and approximately 80% of hydration.

Cell Viability Analysis

LIVE/DEAD® Viability/Cytotoxicity Kit for mammalian cells (Molecular Probe, Invitrogen) was used to determine cell viability in NFAH. The manufacturers protocol was adapted to this aim. Briefly, 2×2 cm pieces were cut and transferred to a Petri dish. Samples were washed three times with PBS. After incubation with solution T during 30 min at room temperature, samples were washed three times and kept in PBS.

The number of live (green) and dead (red) cells was determined by fluorescence microscope. A minimum of four fields for each NFAH section were counted, with at least 100 cells visualized.

Animal Protocol and Hepatic Resection

Wistar male rats with a weight of approximately 250 gr were used for the study. Subcutaneous injection of 80 mg/kg ketamine and 10 mg/kg xylazine induced anesthesia that was maintained with isoflurane inhalation. Animals underwent longitudinal cut from 1 cm below the xiphoid in the craniocaudal direction and median lobe was exposure to proceed.

Hepatic resections were performed in animals with a length of 0.5 or 1.5 cm.

All hemostatic agents applied were given a round shape of 24 mm diameter and were applied on the wound surface by local compression. The time to hemostasis was defined as the arrest of free blood leakage after application of hemostatic agent.

Animals were euthanized one day after surgery to evaluate post-operative hemorrhage, presence of hematoma, migration of the hemostatic agent and intraabdominal adhesion adjacent to the wound. The grade of adhesion was determined by a score of 3 values (0: No adhesion; 1: thin adhesions separable by gravity; 2: thick adhesions no separable by gravity).

The liver was completely excised for liver section/total liver weight ratios calculation. Sections of hepatic tissue attached to the hemostatic agent were fixed in 4% paraformaldehyde for a subsequent histological analysis.

The study was approved by the Research Ethics Committee (REC) of University Hospital Virgen Macarena and Virgen del Rock).

ELISAS

Blood samples were collected with anticoagulant EDTA, centrifuged at 3000 rpm for 5 minutes and kept at −20° C. or −80° C. in small volumes to avoid repeated freeze-thaw cycles.

In order to measure the amount of inflammatory factors, ELISA kits were used following manufacturer's instructions: C Reactive Protein (CRP) (RayBio® Rat CRP ELISA Kit), Interleukin 1 beta (Rat IL-1β ELISA Kit-Elabscience®) y (Rat TNF-α ELISA Kit-CUSABIO®).

Microscopic Analysis

After fixation with 4% paraformaldehyde, paraffin-embedded blocks of liver tissue were cut at 4 micrometres thickness and sections underwent Masson-Trichrome and hematoxylin-eosin staining (Hematoxylin solution—Sigma Aldrich GHS316-500ML; Alcoholic Eosin Y solution—Sigma Aldrich HT110116-500ML; Trichrome Stain (Masson) Kit-Sigma Aldrich HT15-1KT; and Weigert's iron hematoxylin solution HT1079-1set). Sectioned liver samples were analyzed in triplicate in different days.

Figure 11:
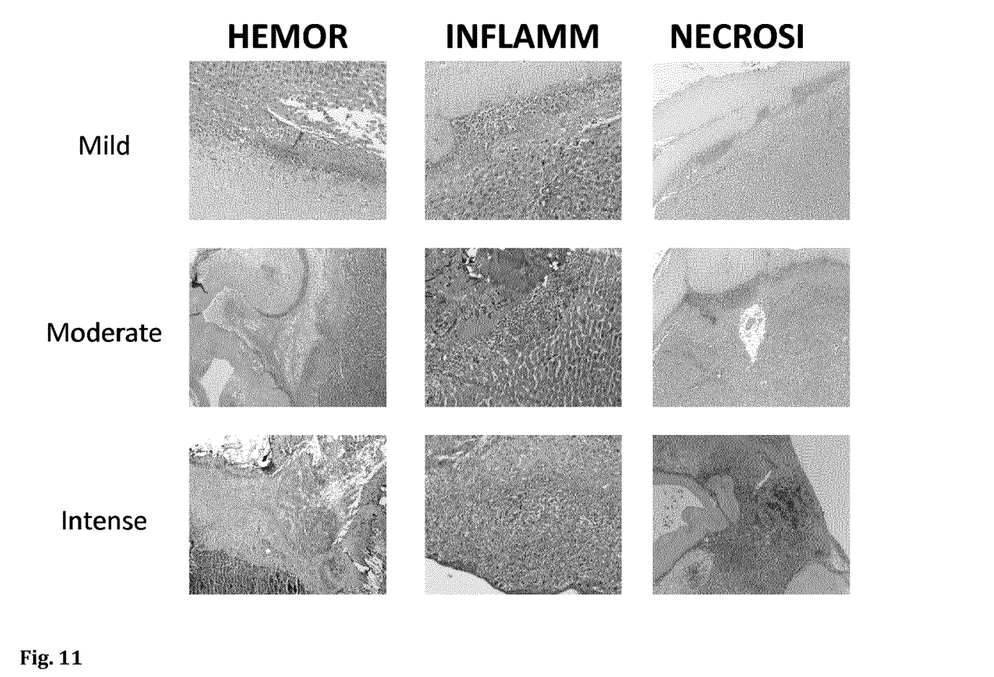
FIG. 11. Examples of hemorrhage, inflammation and necrosis classification.

Histological variables were studied by microscopic analysis and categorized as follow (FIG. 11):

Hemorrhage: Absent (groups of erythrocytes that come together without forming a free zone of hemorrhage); Mild (area of hemorrhage<1 mm diameter); Moderate (area of hemorrhage 1-2.5 mm diameter and less than ×40 high power fields (hpf) of depth); and Intense (area of hemorrhage>2.5 mm diameter or more than ×40 high power fields of depth).

Inflammation: Absent, Mild, Moderate and Intense. Classification was done based on the presence of neutrophil granulocytes per ×40 high power field.

Necrosis: Absent, Mild (0.1-0.4 hpf), Moderate (0.5-1.2 hpf) and Intense (>1.2 hpf).

Statistics

All statistical analyses were performed using GraphPad Prism 5.0 software.

Results

Fabrication of c-NFAH and a-NFAH

Figure 1:
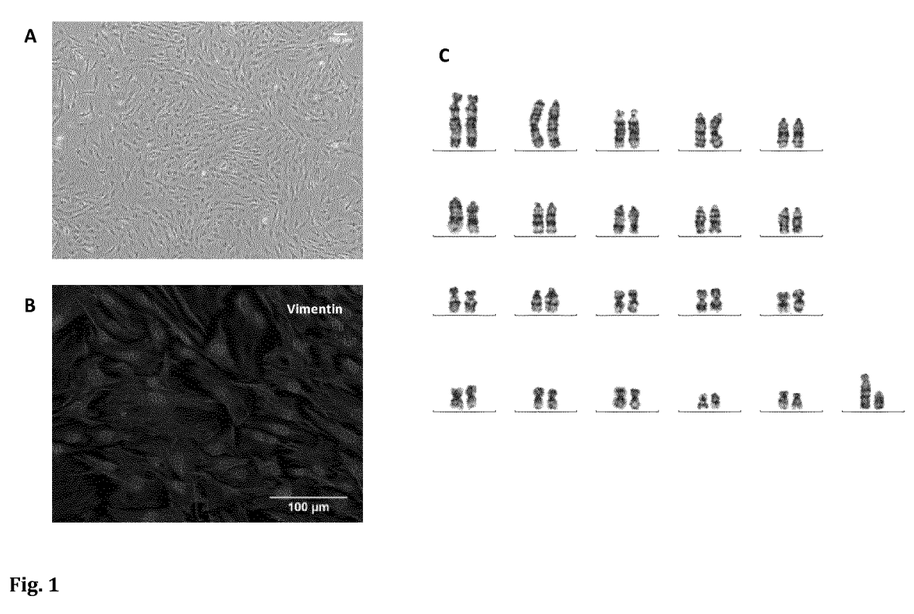
FIG. 1. Characterization of isolated rat fibroblast by collagenase-base technique: (A) Rat fibroblast in culture after isolation; (B) Expression of vimentin was determined by immunostaining analysis in rat fibroblast cultured; HaCat, an immortal keratinocyte cell line was used a negative control; (C) Karyotype analysis of single cell-dissociated culture.

Rat fibroblasts were isolated from skin biopsies by collagenase-based technique. Isolated cells showed vimentin expression and normal karyotype (FIG. 1) as expected for healthy proliferating fibroblasts.

Rat fibroblasts were used for production of c-NFAH (see experimental procedures for details).

NFAH Showed Increased Hemostatic Effect in a Model of Hepatic Resection

Figure 2:
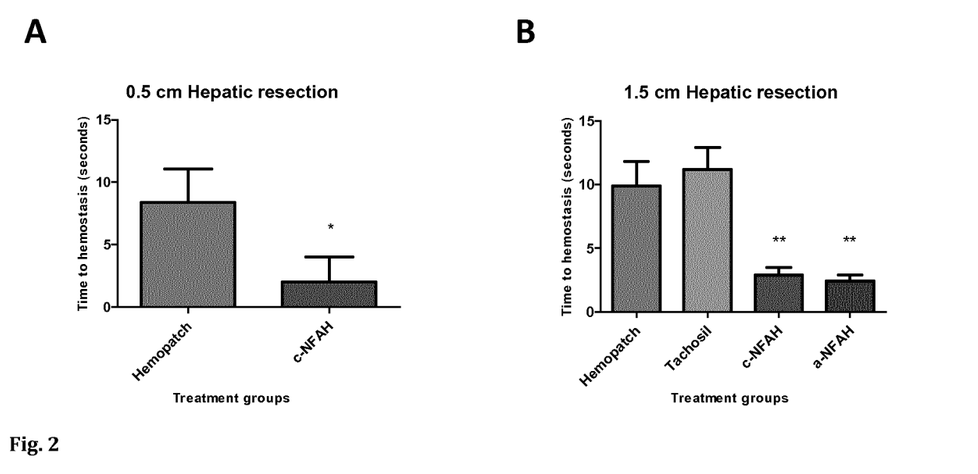
FIG. 2. Time to hemostasis after treatment application. NFAH had superior hemostatic effectiveness relative to Hemopatch and Tachosil. (A): Hemostatic effect in 0.5 cm hepatic resection. (B): Hemostatic effect in 1.5 cm hepatic resection.

This study initially started comparing the hemostatic effect of cellularized NFAH (c-NFAH) versus Hemopatch in a model of 0.5 cm hepatic resection. C-NFAH showed higher hemostasis effectiveness than Hemopatch in 0.5 cm resection (p<0.05) with a mean time to hemostasis equal to 2 sec (N=10, SEM=2, Range=0-20) and 8.4 sec (N=10, SEM=2.6, Range=5-20) respectively (FIG. 2A).

Subsequently, the experiment was expanded to a 1.5 cm hepatic resection that included another two hemostatic agents, acellularized NFAH (a-NFAH) and Tachosil. In the case of 1.5 cm hepatic resection, a-NFAH had the lowest time to hemostasis in the group with 2.4 seconds (N=10, SEM=0.58, Range=1-5), closed to c-NFAH with 2.9 seconds (N=10, SEM=1.72, Range=1-7), both having significantly greater hemostatic success when compared to Hemopatch (9.8 seconds (N=15, SEM=1.02, Range=3-30)) and Tachosil (11.2 seconds (N=10, SEM=0.49, Range=3-17)) (FIG. 2B).

Figure 3:
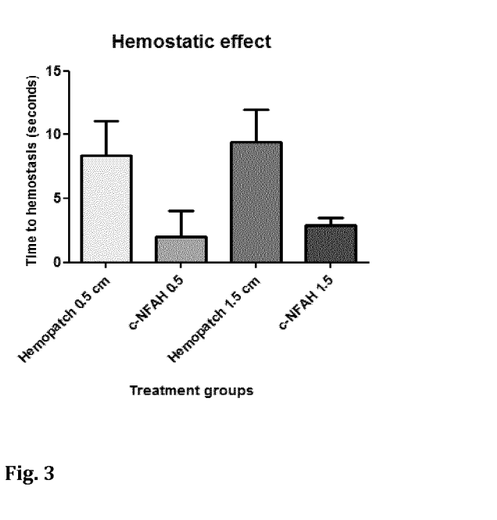
FIG. 3. Comparation of hemostasis in Hemopatch and c-NFAH treatments. Similar results were obtained in term of time to hemostasis for different lengths of liver resection.

Results showed similar time to hemostasis between 0.5 cm and 1.5 cm hepatic resection for c-NFAH and Hemopatch treatments (FIG. 3).

NFAH Showed Easier Applicability

Figure 4:
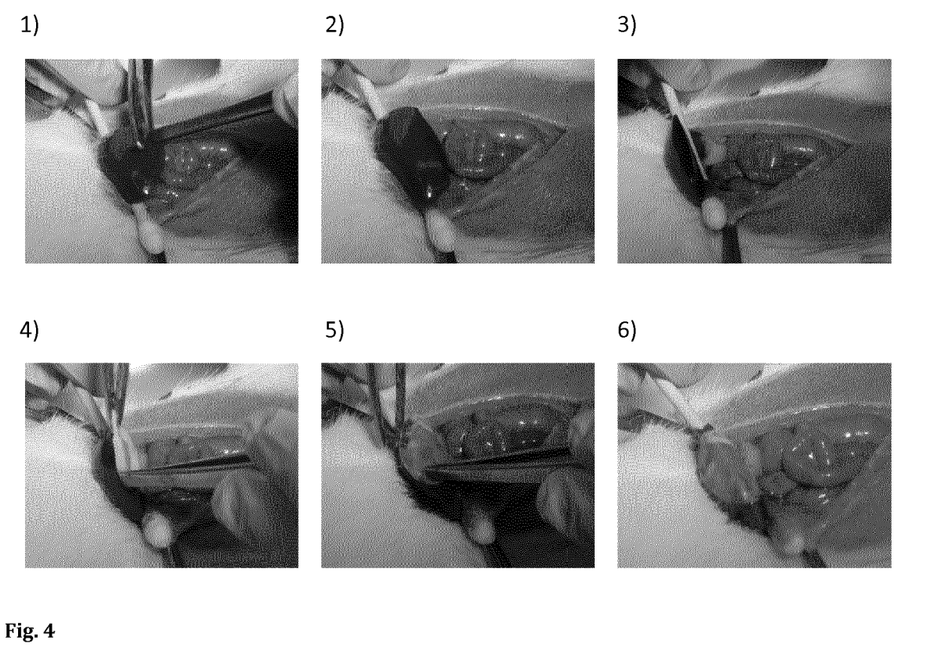
FIG. 4. Sequential application of NFAH in hepatic resection. NFAH had the easiest applicability of treatment groups. 1-3) Hepatic resection and wound exposition. 4-6) NFAH application and final positioning.

Hemopatch and Tachosil were applied by manual compression as indicated by manufacturers. On the contrary, NFAHs were placed on the wound without applying any compression. This application procedure was enough to reach hemostasis with NFAH treatment (FIG. 4).

NFAH Showed Lower Adhesion and Hematomas and No Post-Surgical Rebleeding Nor Migration No presence of hematoma was found in animals treated with c-NFAH in 0.5 cm hepatic resections. By contrast, Hemopatch showed a 40% (FIG. 5A).

Figure 5:
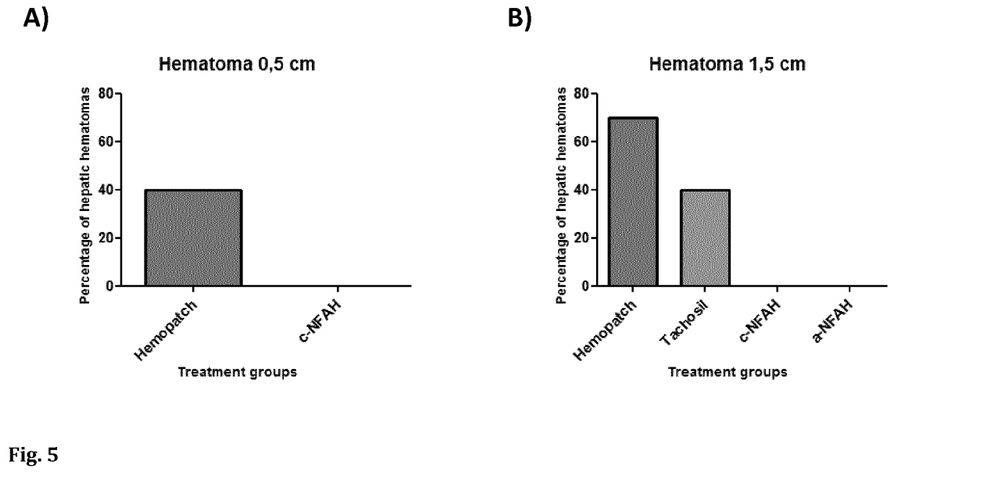
FIG. 5. Bar graph showing the incidence of hematoma. Results showed no presence of hematoma in any cellularized or acellularized NFAH. A) Percentage of animal in 0.5 cm hepatic resection. B) Percentage of animal in 1.5 cm hepatic resection.
Figure 7:
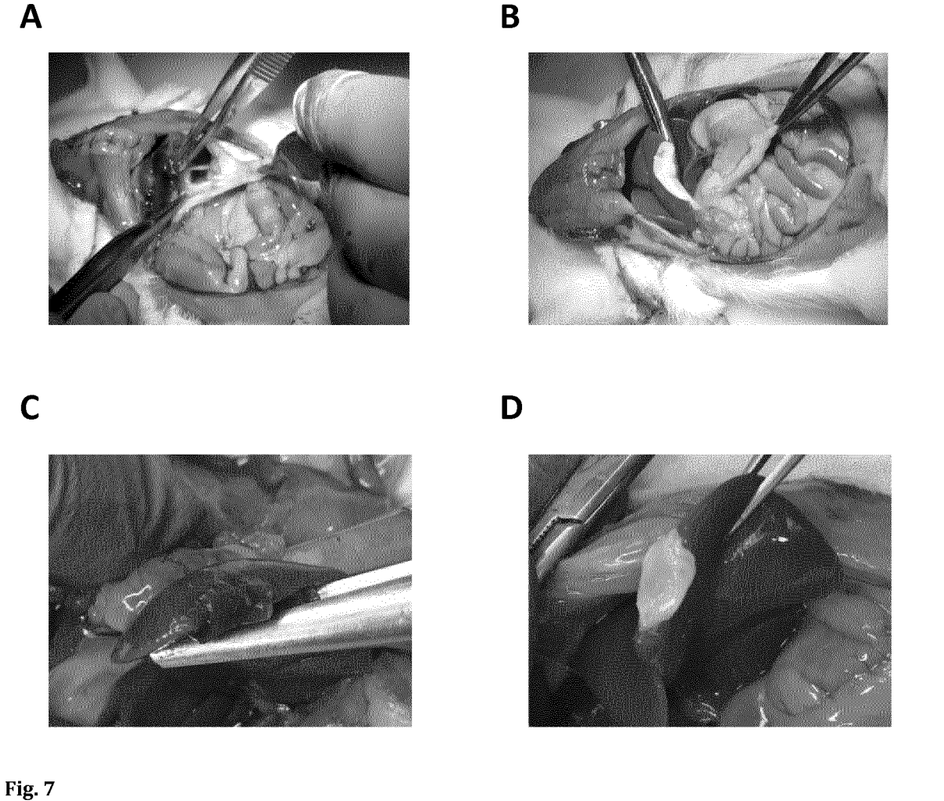
FIG. 7. NFAH showed no presence of hematoma and lower adhesion than other treatments in hepatic resection 24 hours after application. (A): Hemopatch causing high grade of adhesion. (B): NFAH showing no adhesion. (C): Presence of hematoma in Hemopatch treatment. (D): No presence of hematoma in NFAH treatments.

In 1.5 cm hepatic resection, C-NFAH and a-NFAH showed no incidences of hematoma while Hemopatch and Tachosil had 73.3% and 40% respectively (FIGS. 5B and 7C-D).

Figure 6:
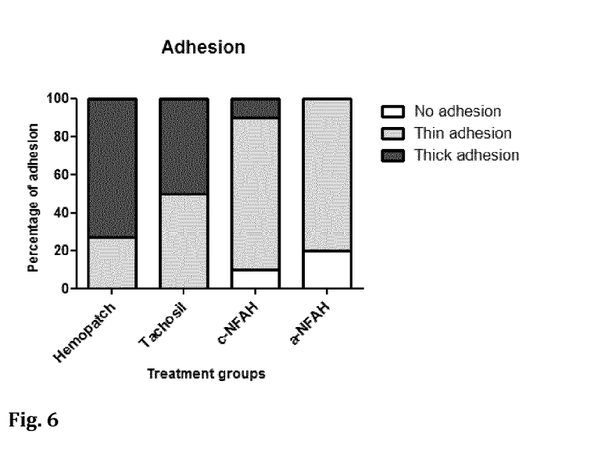
FIG. 6. Percentage of grade of adhesion. NFAH showed lower adhesion than other treatments in hepatic resection 24 hours after application. The grade of adhesion was determined by next ranking: No adhesion (separate anatomical structures); Thin adhesions (adhesion separable by gravity); Thick adhesions (adhesion no separable by gravity).

Undesired adhesion to tissues was estimated on the sacrifice. Results showed significant differences among the groups. C-NFAH and a-NFAH had similar results with most of the animal showing thin adhesion. However, Hemopatch and Tachosil showed more evident adhesion to adjacent organs (Table 1 and FIGS. 6 and 7A-B).

TABLE 1

Effectiveness of fibrin-agarose hydrogels in preventing peritoneal adhesions in rats

|  | a-NFAH | c-NFAH | Hemopatch ® | Tachosil ® |
|---|---|---|---|---|
| Score 2 | 0 | 1 | 11 | 5 |
| Score 1 | 8 | 8 | 4 | 5 |
| No adhesion | 2 | 1 | 0 | 0 |
| N | 10 | 10 | 15 | 10 |

Table 1: Number of rats by treatment group and grade of adhesion. A-NFAH and c-NFAH showed similar lower adhesion relative to Hemopatch and Tachosil. The grade of adhesion was determined by a score of 3 values (No adhesion: separate anatomical structures; Score 1: thin adhesions separable by gravity; Score 2: thick adhesions no separable by gravity).

Figure 8:
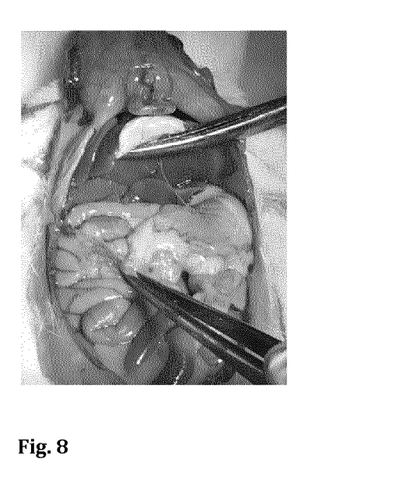
FIG. 8. NFAH showed neither rebleeding nor migration in hepatic resections 24 hours after application.

After 24 hours of hemostasis achievement, no presence of rebleeding was found in any treated group (FIG. 8) and only one Tachosil pad seemed to migrate in a rat (probably was moved during suture).

NFAH Showed No Higher Inflammatory Response than Hemopatch and Tachosil

Figure 9:
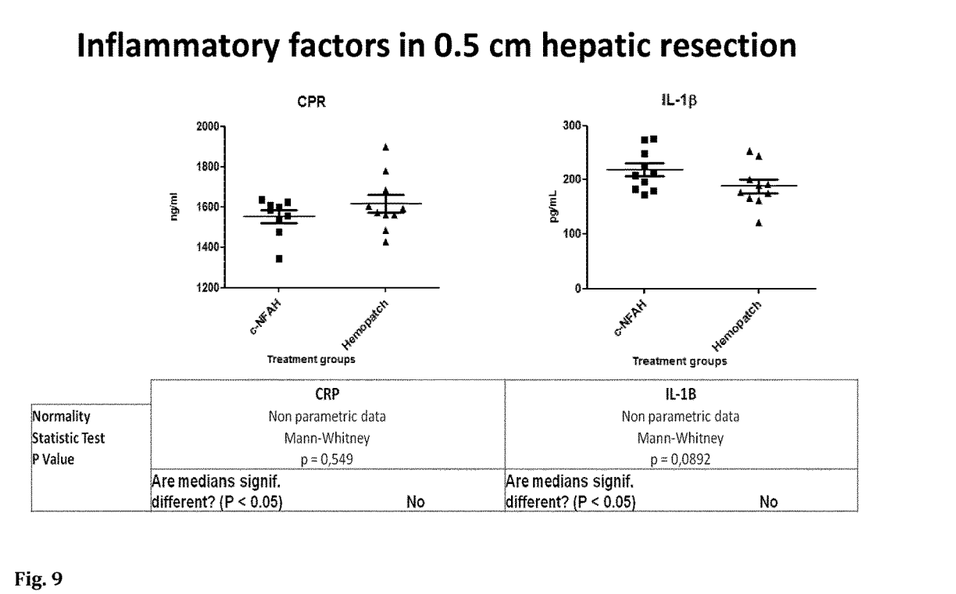
FIG. 9. Inflammatory factors in animals with 0.5 cm hepatic resection after 24 hours. There were no significant differences of C-reactive protein and IL-16 between cellularized NFAH and Hemopatch treatments.
Figure 10:
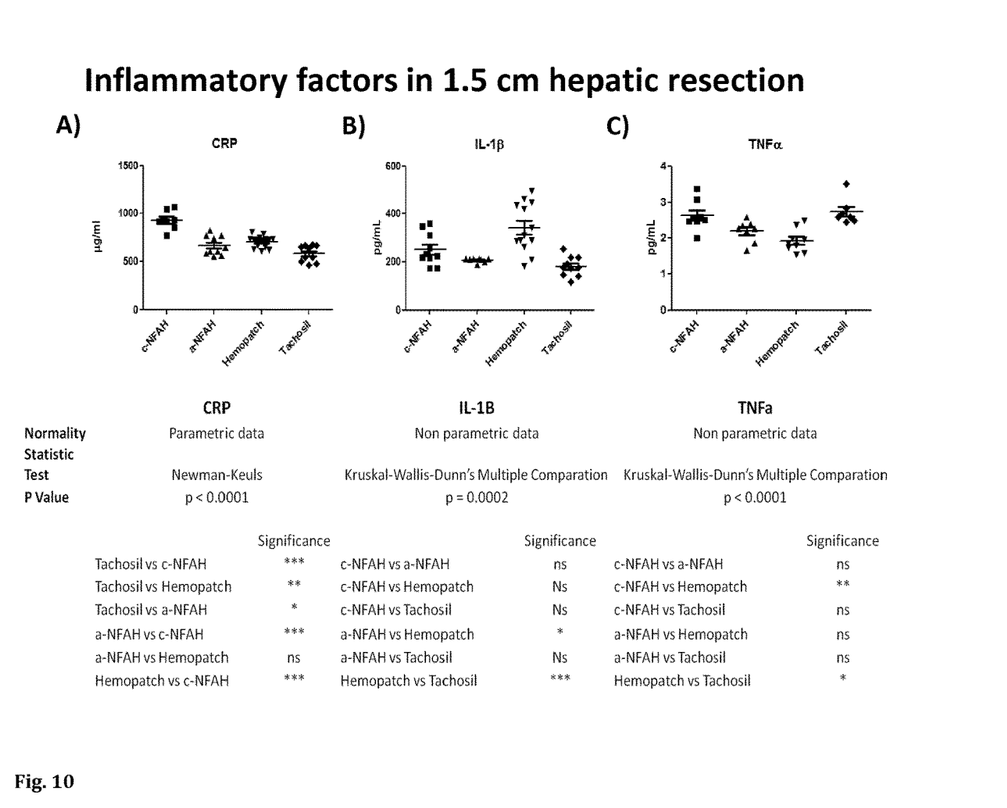
FIG. 10. Inflammatory factors in animals with 1.5 cm hepatic resection after 24 hours. (A) A-NFAH treatment showed no significant difference in levels of CRP inflammatory factor than Hemopach and Tachosil treatments. (B) Hemopatch treatment caused higher levels of IL-1β inflammatory factors than a-NFAHs treatments. (C) A-NFAH showed no significant difference of TNF-α inflammatory level in respect to either Hemopatch or Tachosil.

The levels of inflammatory factors for 0.5 cm and 1.5 cm hepatic resections are shown in FIGS. 9 and 10 respectively. A minimum of six animals were considered in each treated group.

Figure 12:
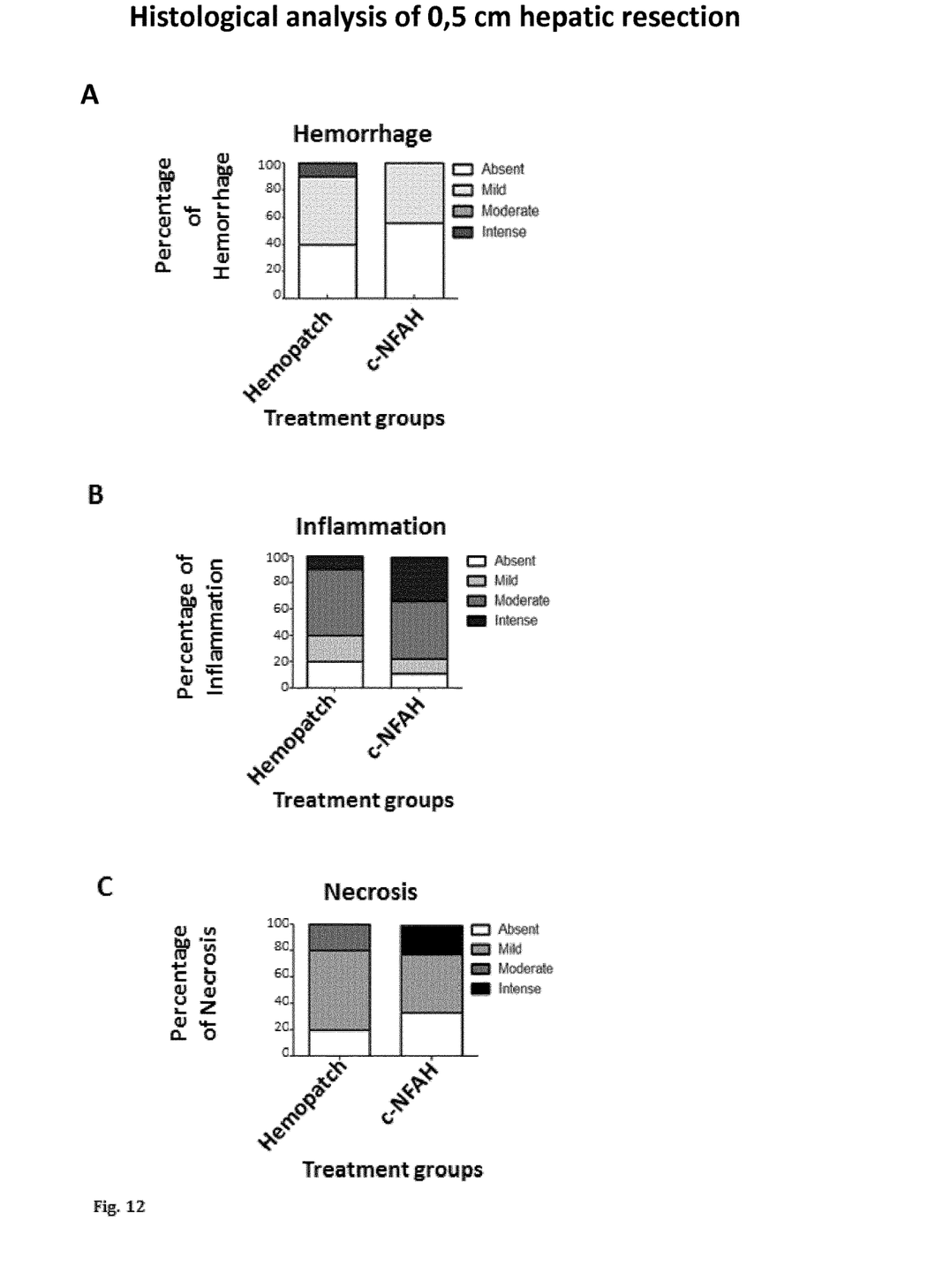
FIG. 12. Bar graphs showing percentage of hemorrhage, inflammation and necrosis in 0.5 and 1.5 cm hepatic resections after treatment with hemostatic agents. Each sample was classified in absent, mild, moderate or intense (see methods for classification). (A-C): Histological analysis of 0.5 cm hepatic resection; (D-F): Histological analysis of 1.5 cm hepatic resection.

NFAH Treatments had Better Results in Histological Analysis for Longer Hepatic Resections Variables of microscopic analysis were categorized as previously indicated in materials and methods (FIG. 11 shows examples of classification). Histological analysis of 0.5 cm hepatic resections showed lower presence of hemorrhage in c-NFAH treatment. However, inflammatory response and necrosis was higher than Hemopatch treatment (FIG. 12A-C). These results differ with 1.5 cm hepatic resections which showed lower inflammatory response and necrosis in NFAH treatments. Moreover, c-NFAH treatment had the lowest presence of hemorrhage (FIG. 12D-F).

The invention claimed is:

1. A method for controlling bleeding or promoting hemostasis in a wound, or sealing biological tissue, comprising applying a composition to the wound or biological tissue, wherein the composition comprises a hydrogel comprising fibrin and agarose.

2. The method according to claim 1, wherein the wound results from laparotomy or laparoscopic surgery, orthopedic surgery, or trauma.

3. The method according to claim 1, wherein the hydrogel comprising fibrin and agarose further comprises cells.

4. The method according to claim 3, wherein the hydrogel comprising fibrin and agarose further comprises fibroblasts.

5. The method according to claim 1, wherein the hydrogel comprising fibrin and agarose does not comprise cells.

6. The method according to claim 1, wherein the agarose is type VII agarose.

7. The method of claim 2, wherein the trauma results from spleen laceration or hepatic surgery.

8. The method according to claim 3, wherein the agarose is type VII agarose.

9. The method according to claim 4, wherein the agarose is type VII agarose.

10. The method according to claim 1, wherein the hydrogel comprising fibrin and agarose is nanostructured.

11. The method according claim 1, wherein the hydrogel comprising fibrin and agarose is not nanostructured.

12. The method according to claim 1, wherein the wound is a large-bed wound.

13. The method according to claim 1, wherein the composition is applied with compression.

14. The method according to claim 1, wherein the composition is applied without compression.

* * * * *